(12) United States Patent
Linden et al.

(10) Patent No.: US 10,124,107 B2
(45) Date of Patent: Nov. 13, 2018

(54) CLEANING OF BIOLOGICAL FLUID

(71) Applicant: GAMBRO LUNDIA AB, Lund (SE)

(72) Inventors: Torbjorn Linden, Hasslo (SE); Husam Mohammed, Malmo (SE)

(73) Assignee: Gambro Lundia AB, Lund (SE)

( * ) Notice: Subject to any disclaimer, the term of this patent is extended or adjusted under 35 U.S.C. 154(b) by 458 days.

(21) Appl. No.: 14/651,810

(22) PCT Filed: Dec. 13, 2013

(86) PCT No.: PCT/EP2013/076574
§ 371 (c)(1),
(2) Date: Jun. 12, 2015

(87) PCT Pub. No.: WO2014/091002
PCT Pub. Date: Jun. 19, 2014

(65) Prior Publication Data
US 2015/0306297 A1     Oct. 29, 2015

Related U.S. Application Data

(60) Provisional application No. 61/737,262, filed on Dec. 14, 2012.

(30) Foreign Application Priority Data

Dec. 14, 2012  (SE) ...................... 1251426

(51) Int. Cl.
*A61M 1/34*   (2006.01)
*A61M 1/36*   (2006.01)
*A61M 1/16*   (2006.01)

(52) U.S. Cl.
CPC ............ *A61M 1/3486* (2014.02); *A61M 1/16* (2013.01); *A61M 1/3472* (2013.01);
(Continued)

(58) Field of Classification Search
CPC .................................................. A61M 1/3486
See application file for complete search history.

(56) References Cited

U.S. PATENT DOCUMENTS 4,401,430 A   8/1983   Dorson
4,702,841 A   10/1987  Sengbusch
(Continued)

FOREIGN PATENT DOCUMENTS

CN   1087914 A    12/1992
CN   1143334      2/1997
(Continued)

OTHER PUBLICATIONS

PCT/EP2013/076574 International Search Report and Written Opinion dated Feb. 27, 2014 (11 pages).
(Continued)

*Primary Examiner* — Peter Keyworth
(74) *Attorney, Agent, or Firm* — Mueting, Raasch & Gebhardt, P.A.

(57) ABSTRACT

The present invention relates to removal of protein bound deleterious substances from an extracorporeal biological fluid by changing the affinity of the substance to the protein. The invention relates to the use of displacer substances for removal of deleterious substances. The present invention also relate to a method of removal, a system, a cleaning fluid comprising the displacer substances for removal of deleterious substances.

5 Claims, 5 Drawing Sheets

— Measured amount of p-cresol with Sodium salicylate as displacer substance.

(52) U.S. Cl.
CPC ........... *A61M 1/3687* (2013.01); *A61M 1/369* (2013.01); *A61M 2202/0042* (2013.01); *A61M 2202/07* (2013.01)

(56) References Cited

U.S. PATENT DOCUMENTS

| | | | |
|---|---|---|---|
| 5,536,412 | A | 7/1996 | Ash |
| 5,944,684 | A | 8/1999 | Roberts |
| 7,351,800 | B2 | 4/2008 | Otagiri |
| 7,615,158 | B2 | 11/2009 | Sternby |
| 8,206,591 | B2 | 6/2012 | Kotanko |
| 8,834,400 | B2 | 9/2014 | Houwen |
| 8,877,711 | B2 | 11/2014 | Kiessling |
| 2005/0082225 | A1 | 4/2005 | Kreymann |
| 2009/0139930 | A1 | 6/2009 | Sternby |
| 2011/0184377 | A1* | 7/2011 | Ward ............... A61K 31/60 604/500 |
| 2012/0226258 | A1 | 9/2012 | Otto |
| 2012/0253022 | A1 | 10/2012 | Kotanko |

FOREIGN PATENT DOCUMENTS

| | | |
|---|---|---|
| CN | 1638788 A | 7/2005 |
| CN | 101827619 | 9/2010 |
| CN | 101927011 A | 12/2010 |
| CN | 102725008 | 10/2012 |
| DE | 3004990 | 10/1981 |
| DE | 3527411 | 2/1987 |
| EP | 0102564 | 3/1984 |
| EP | 0966980 | 12/1999 |
| EP | 1323440 | 7/2003 |
| WO | WO 01/58496 | 8/2001 |
| WO | WO 2007/046757 | 4/2007 |
| WO | WO 2007/079886 | 7/2007 |

OTHER PUBLICATIONS

De Loor, Henriette, "Sodium Octanoate to Reverse Indoxyl Sulfate and *p*-cresyl Sulfate Albumin Binding in Uremic and Normal Serum During Sample Preparation Followed by Fluorescence Liquid Chromatography," *Journal of Chromatograph A*, 1216 (2009) 4684-3688.

Klammt, Sebastian et al., "Increase of Octanoate Concentrations During Extracorporeal Albumin Dialysis Treatments," *Therapeutic Apheresis and Diaylsis*, 13(5):437-443 (2009).

Mabuchi, Hisao et al., "Displacement by Anionic Drugs of Endogenous Ligands Bound to Albumin in Uremic Serum," *Therapeutic Drug Monitoring*, 10:261-264 (1988).

Barreto et al., "Serum Indoxyl Sulfate is Associated with Vascular Disease and Mortality in Chronic Kidney Disease Patients," *Clin. J. Am. Soc. Nephrol.*, 2009, 4:1551-1558.

Beare-Rogers et al., "Lexicon of Lipid Nutrition (IUPAC Technical Report)," *Pure and Applied Chemistry*, 2001, 73:685-744.

Enomoto et al., "Roles of Organic Anion Transporters in the Progression of Chronic Renal Failure," *Ther. Apher Dial.*, 2007, 11:27-31.

Hoshimito et al., "Caprylic Acid and Medium-Chain Triglycerides Inhibit IL-8 gene Transcription in Caco-2 Cells: Comparison with the Potent Histone Deacetylase Inhibitor Trichostatin A," *British Journal of Pharmacology*, 2002, 136-280-6.

Meijers et al., "A Review of Albumin Binding in CKD," *Am. J. Kidney Dis.*, 2008, 51:839-850.

Meijers et al., "*p*-Cresol and Cardiovascular Risk in Mild-to-Moderate Kidney Disease," *Clin. J. Am. Soc. Nephrol.*, 2010, 5:1182-1189.

Noctor et al., "Allosteric and Competitive Displacement of Drugs from Human Serum Albumin by Octanoic Acid, as Revealed by High-Performance Liquid Affinity Chromatography, on a Human Serum Albumin-Based Stationary Phase," *Journal of Chromatography*, 1992, 577:305-15.

Sakai et al., "Interaction Mechanism Between Indoxyl Sulfate, a Typical Uremic Toxin Bound to Site II, and Ligands Bound to Site I of Human Serum Albumin," *Pharmaceutical Research*, 2001, 18:520-524.

www.chemspider.com/chemical-structure.15307.html Retrieved on Dec. 10, 2015.

* cited by examiner

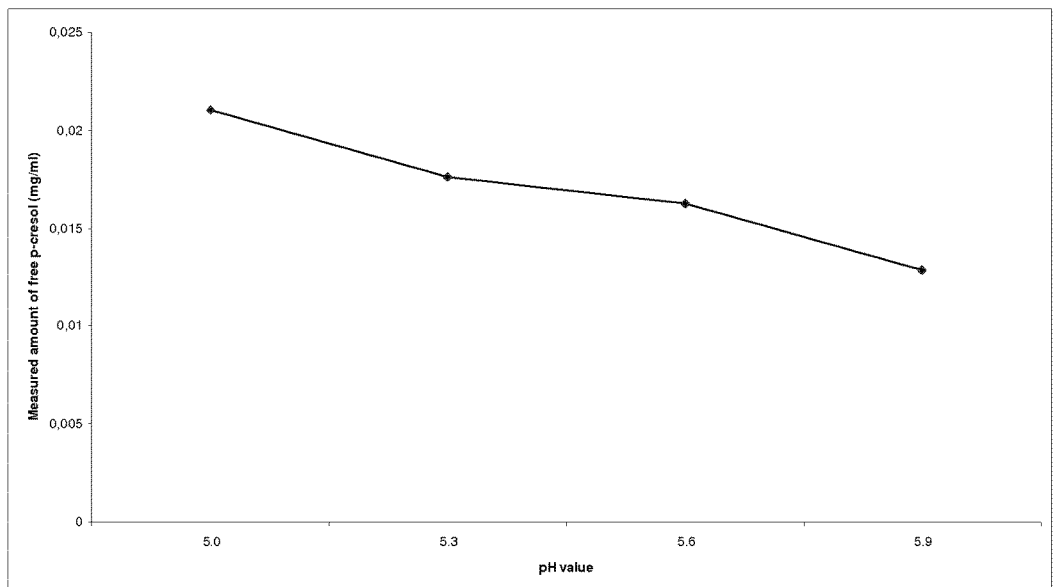
Figure 1a – Measured amount of p-cresol with Sodium salicylate as displacer substance.
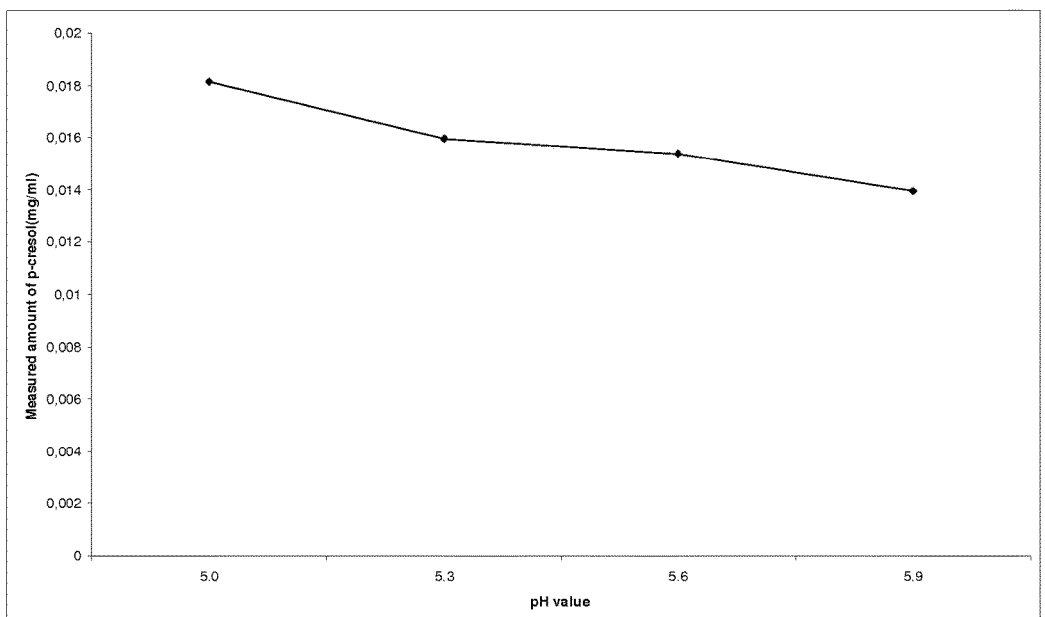
Figure 1b - Measured amount of p-cresol with Sodium acetylsalicylate as displacer substance.

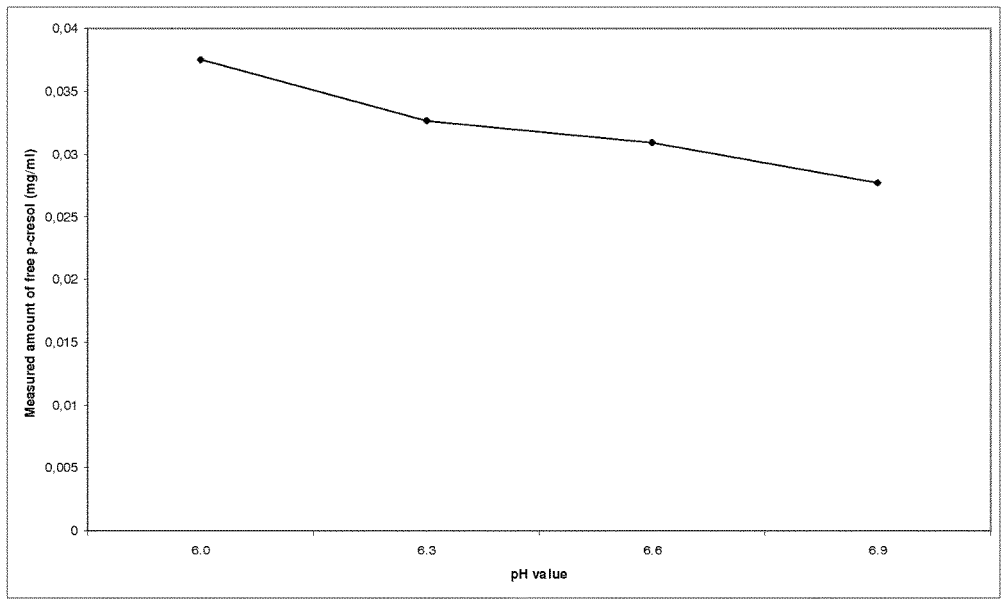
Figure 1c – Measured amount of p-cresol with Sodium octanoate as displacer substance.
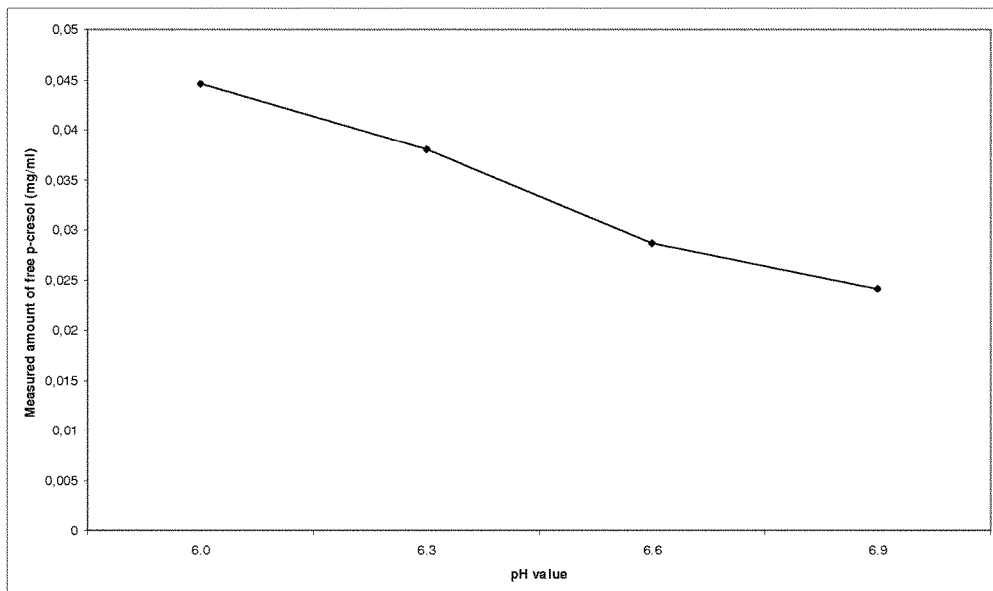
Figure 1d – Measured amount of p-cresol with a combination of Sodium octanoate and Sodium salicylate as displacer substances.

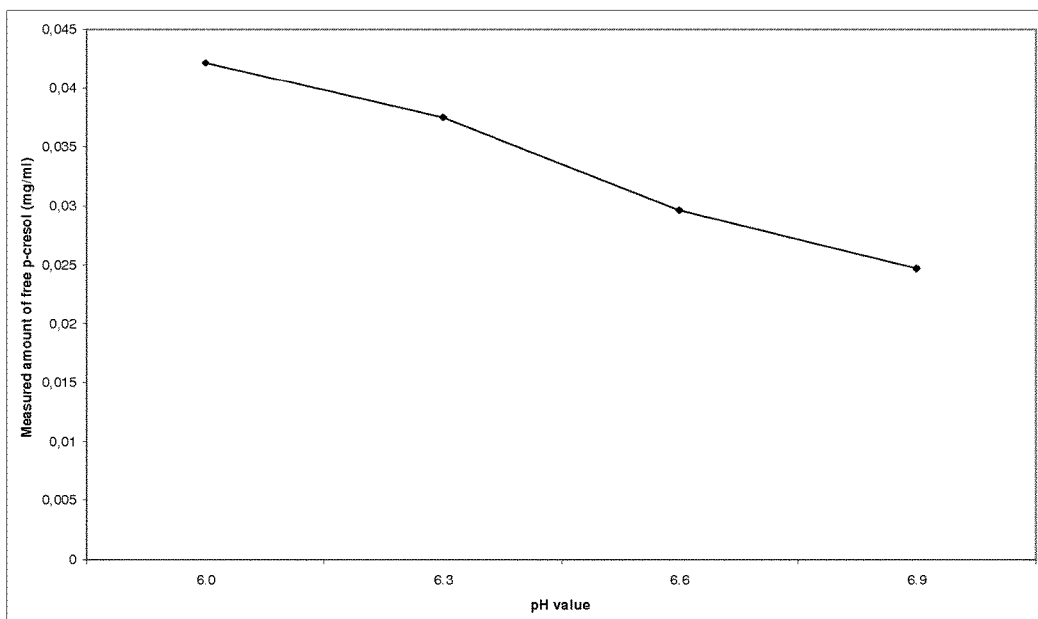
Figure 1e - Measured amount of p-cresol with a combination of Sodium octanoate and Sodium acetylsalicylate as displacer substances.

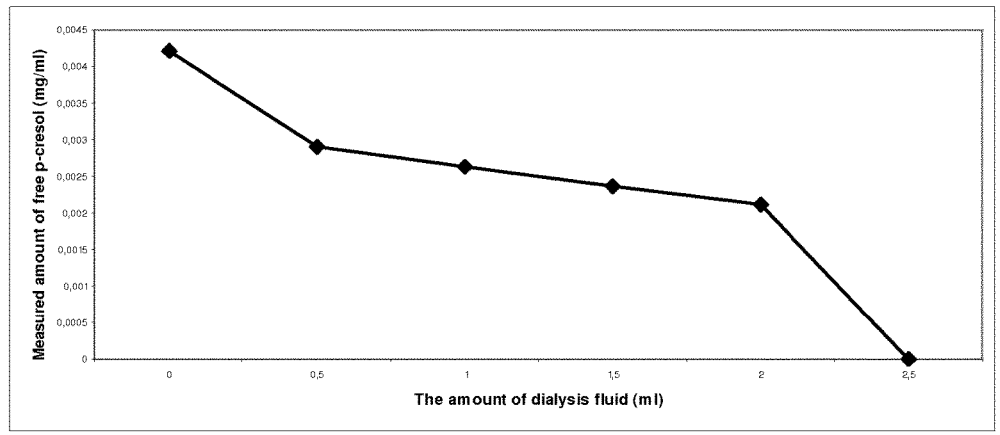
Figure 2a - Result of addition of dialysis solution at pH 8 and room temperature.
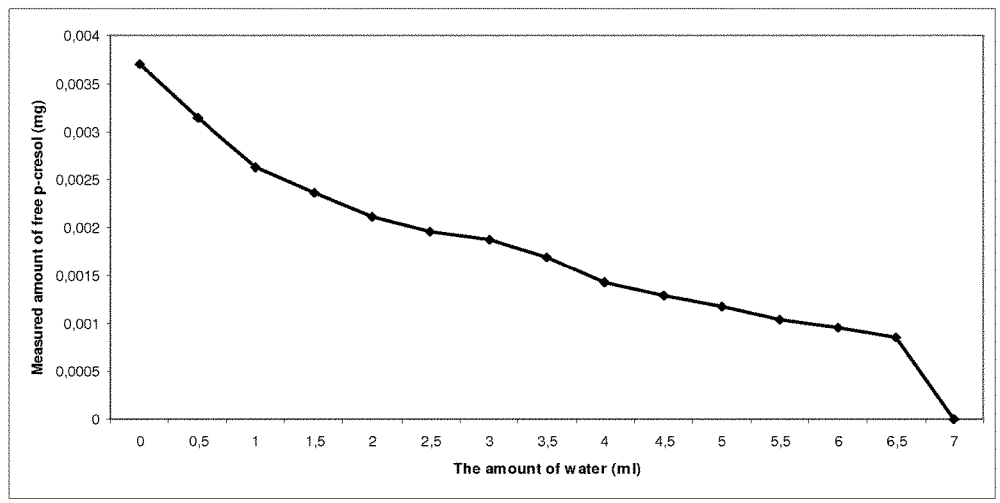
Figure 2b - Result of addition of water at pH 8 and 37 degrees Celsius.

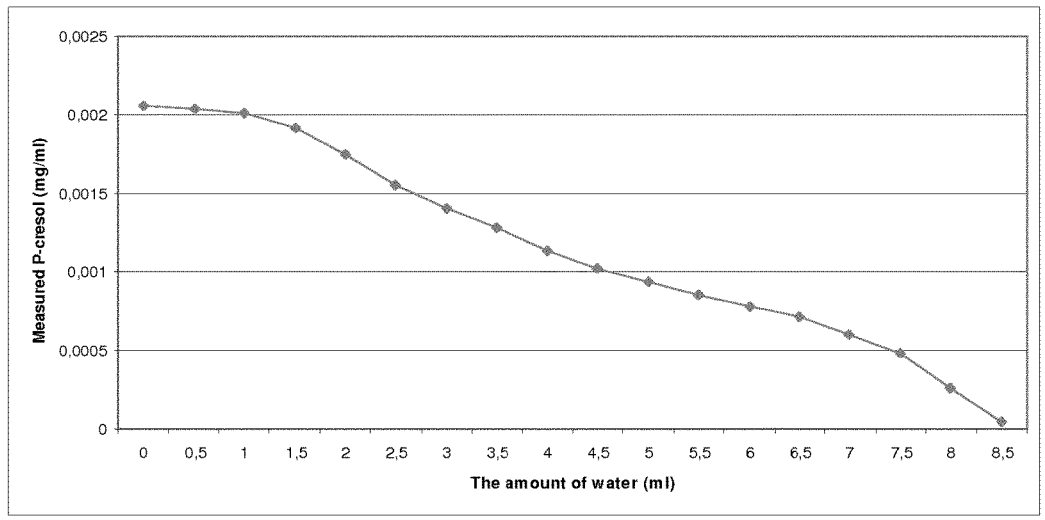
Figure 2c - Result of addition of water at pH 8 and room temperature.
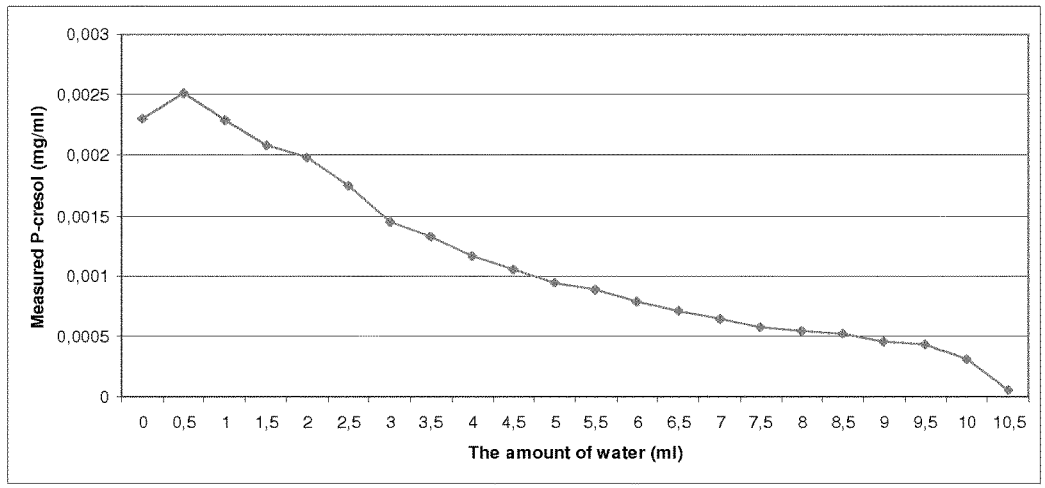
Figure 2d - Result of addition of water at pH 8 and 50 degrees Celsius.

CLEANING OF BIOLOGICAL FLUID

This application is the U.S. National Stage Application of International Application No. PCT/EP2013/076574, filed Dec. 13, 2013 and which was published in English on Jun. 19, 2014 as International Publication No. WO 2014/091002 A1, which claims the benefit under 35 U.S.C. 119(e) of U.S. Provisional Application No. 61/737,262 filed Dec. 14, 2012. International Application No. PCT/EP2013/076574 also claims priority to Sweden Application No. 1251426-1 filed Dec. 14, 2012. All of these documents are incorporated herein by reference in their entirety.

TECHNICAL FIELD

The present invention relates to removal of protein bound deleterious substances from a biological fluid by changing the affinity of the substance to the protein. Moreover, the invention relates to use of $C_5$-$C_{10}$-fatty acid or salts thereof, or salicylic acid, or derivatives thereof, or salts thereof, as a displacer substance of the deleterious substances. The present invention also relate to a method of removal, a system, a cleaning fluid comprising the displacer substances for removal of deleterious substances.

BACKGROUND OF THE INVENTION

The kidney function of the human body may failure for different reasons. The kidney has different functions which are crucial for survival, such as separation and transportation of waste products from the biological fluid e.g. blood, balancing the level of electrolytes in the body, and balancing the acid and base status in the body.

Failure of the kidney may be acute or chronic, and may be treated by different methods like transplantation of the organ or by dialysis treatment. In dialysis treatment the biological fluids are separated from the body and treated as extracorporeal fluid outside the human body. There are different methods of dialysis available, for example hemodialysis, hemofiltration, and hemodiafiltration. In common, they all clean the body from waste products like urea and deleterious compounds like uremic toxins.

Deleterious compounds, like protein bound toxins, may be present in different biological fluids like, for example, blood, blood plasma, peritoneal fluids. A part of the deleterious compounds bind to proteins present in the blood, such as albumins. The uremic toxins are in normal cases removed from the biological fluids by the kidney function, as well as by the liver function. However, there may be sitvations where the deleterious substances shall be removed from the biological fluid, and where this removal process shall take place external the human body. For example, the blood extracted from the body during dialysis treatment, should also be cleaned from deleterious compounds.

There are methods and means available for removal of the deleterious compounds. An apparatus for cleaning of extracorporeal blood is known from WO 2007/046757. In this apparatus the blood is fractioned into a first cleaned fraction and a second cleaned fraction. The second cleaned fraction is produced by removing toxins bound on proteins and/or toxins dissolved in the plasma.

In U.S. Pat. No. 7,615,158 B2 it is described a method for removing partially carrier bound substances from blood. The method described therein includes applying a pressure gradient across the membrane to create an ultrafiltration.

A method for removal of uremic toxins bound to albumin in blood of a patient is described in U.S. Pat. No. 8,206,591 B2. This method includes introducing a displacer substance into the blood such that the displacer substance displaces deleterious substances bound to the albumin. The unbound uremic toxins are then removed by extracorporeal renal displacement treatment before the blood is returned to the patient. The displacer substance is for example bilirubin. This method is suggested to be used when drugs, such as salicylate shall be removed from the blood.

However, there is a need to improve the possibilities to remove the deleterious compounds from the biological fluids. Therefore, further means are needed to separate and clean the extracorporeal biological fluids from uremic toxins.

SUMMARY OF THE INVENTION

One object of the present invention is to provide a use and a method of removing deleterious substances from an extracorporeal biological fluid. As the deleterious substances are substances executing a negative effect on the physiological functions of the body when present therein, it is a desire to remove these substances.

Another object of the invention is to provide a system, for removing deleterious substances from a biological fluid by the method defined herein.

Also, one object of the invention is to provide a cleaning fluid comprising one or more of the displacer substances described herein.

In one embodiment of the invention is a use of a substance selected from $C_5$-$C_{10}$-fatty acid, or derivatives thereof, or salts thereof; and salicylic acid, derivatives thereof, or salts thereof; or combinations thereof, as displacer substance for removing a deleterious substance bound to a protein in an extracorporeal biological fluid provided.

The use of a displacer substance for removing a deleterious substance bound to a protein in an extracorporeal biological fluid, wherein the displacer substance is selected from $C_5$-$C_{10}$-fatty acid, or derivatives thereof, or salts thereof, salicylic acid, or derivatices thereof, or salts thereof, or acetylsalicylic acid, or salts thereof; or combinations thereof, is to obtain a change of affinity of the deleterious substance to the protein.

Another embodiment is a displacer substance for use in treatment of extracorporeal biological fluids wherein the treatment is removal of deleterious substances bound to proteins present in the biological fluid by using a displacer substance selected from $C_5$-$C_{10}$-fatty acid, or derivatives thereof, or salts thereof, salicylic acid, or derivatives thereof, or salts thereof, or acetylsalicylic acid, or salts thereof; or combinations thereof.

Another embodiment is the use of displacer substance $C_5$-$C_{10}$-fatty acid, or derivatives thereof, or salts thereof. A further embodiment is the use of displacer substance salicylic acid, derivatives thereof, or salts thereof.

In one embodiment of the invention a use of salicylic acid and derivatives thereof, or salts thereof, as displacer substance to remove a deleterious substance bound to a protein is illustrated.

An advantage with salicylic acid and derivatives, and salts thereof is its capability to bind to different sites of the albumin, with both competitive and allosteric binding effect. Therefore by changing the affinity of the deleterious substance by changing the conformity of the protein it is possible to replace or displace the deleterious substance with the displacer substance.

The displacer substance acts on the protein by competitive protein binding, or by allosteric binding, or by combination of both and by that changing the affinity to the protein. Thus by elaborating with the affinity of the molecules binding to the protein it has been shown that the affinity of the deleterious substances may be decreased and be displaced of replaced by the displacer substances. This is especially useful when the deleterious substance comprises an uremic toxin.

In one embodiment the deleterious substance to be removed is an uremic toxin of the group comprising the compounds p-cresol; p-cresyl sulfate; indoxyl sulfate; CMPF; and combinations thereof.

In one embodiment the protein which the deleterious substance binds to is an albumin, such as serum albumin.

In one embodiment illustrating the invention the displacer substance is a combination of salicylic acid, derivatives thereof, or salts thereof in combination with one or more $C_5$-$C_{10}$-fatty acids.

In another embodiment of the invention the displacer substance is selected from salicylic acid, derivatives thereof, or salts thereof, for example acetyl salicylic acid.

In one embodiment of the invention a method of removing a deleterious substance from an extracorporeal biological fluid is provided. The deleterious substance binds to a protein. The method comprises the following steps:

a) introducing a displacer substance into the biological fluid under conditions in which the displacer substance displaces or replaces deleterious substance bound to the protein, thereby resulting in additional unbound deleterious substances in the biological fluid; and b) removing unbound deleterious substance from the biological fluid; wherein said displacer substance is selected from $C_5$-$C_{10}$-fatty acid, or derivatives thereof, or salts thereof; and salicylic acid, derivatives thereof, or salts thereof; or combinations thereof; preferably selected from salicylic acid, or salts thereof, acetyl salicylic acid, or salts thereof, and a $C_8$-fatty acid, or salts thereof, or combinations thereof, more preferably a combination of salicylic acid and $C_8$-fatty acid, or salts thereof.

The biological fluid may be any biological fluid comprising deleterious substances which are able to bind to a protein. The biological fluid is an extracorporeal biological fluid which is to undergo treatment by removal of deleterious substances. Examples of biological fluids are blood, plasma, and peritoneal fluid. This list is not exhaustive.

In one embodiment the method according to step a) and step b) is performed at temperature between 30 and 60 degrees Celsius, preferably between 35 and 50 degrees Celsius.

Another embodiment of the illustrated invention is a method according to the above wherein step a) and step b) are performed at pH between 5 and 8, preferably at pH between 5 and 6.

In another embodiment of the invention the removal of the deleterious substances according to step b) is performed by dialysis, electrodialysis, or plasmapheresis.

Also, another embodiment of the invention is a cleaning fluid comprising one or more displacer substances. The displacer substances may be selected from $C_5$-$C_{10}$-fatty acids or salts thereof, or salicylic acid, or derivatives thereof, or salts thereof; or combinations thereof, preferably selected from salicylic acid, or salts thereof, acetyl salicylic acid, or salts thereof, and a $C_8$-fatty acid, or salts thereof, or combinations thereof.

A still further embodiment of the invention is a system configured to remove deleterious substances from blood. The system comprises a blood circuit, a fluid circuit and a blood treatment unit comprising a filter system including one or more semipermeable membranes separating a fluid compartment from a blood compartment, provided with means for mixing blood and a cleaning fluid and directing the mixture obtained through said blood compartment, wherein the cleaning fluid comprises displacer substances to remove said deleterious substances bound to protein. The displacer substances are selected from $C_5$-$C_{10}$-fatty acids or salts thereof; salicylic acid, or derivatives thereof, or salts thereof; or combinations thereof. For example, displacer substances are selected from $C_5$-$C_{10}$-fatty acids or salts thereof; salicylic acid, or salts thereof; and acetylsalicylic acid acid, or salts thereof; or combinations thereof.

Optionally, the system is equipped with an additional unit wherein the biological fluid, for example blood, is separated in a first fraction of blood cells, and a second fraction of plasma. To the second fraction is a displacer substance added for removal of the deleterious substances.

The displacer substances of the invention may be selected from $C_5$-$C_{10}$-fatty acids, or derivatives thereof, or salts thereof; or salicylic acid, or derivatives thereof, or salts thereof; or combinations thereof. Preferably, the displacer substance is selected from sodium salicylate, sodium acetylsalicylate, and sodium octanoate (sodium salt of a $C_8$-fatty acid), or combinations thereof.

An additional advantage to use salicylic acid and derivatives and salt thereof as displacer substance for removing deleterious molecules from biological fluids like blood is that they have antithrombogenic and anticoagulative properties. Otherwise, when the biological fluid is blood, an anticoagulating agent must be added separately to avoid clotting and coagulation of blood. The antithrombogenic and anticoagulative effect may be as a separate effect or as an additional effect to the previous.

It is well known that salicylic acid, derivatives thereof, and salts thereof, has antioxidative and anti-inflammatory properties. These substances have also effects against diseases and syndromes like chronic inflammation, arteriosclerosis and atherosclerosis.

It has surprisingly been found that salicylic acid, derivatives thereof, and salts thereof as well as $C_5$-$C_{10}$-fatty acids are useful for removal of deleterious substances from extracorporeal biological fluids.

The surprisingly findings that the displacer substances have an effect on the binding sites of albumin is an advantage for using these substances in dialysis treatment and plasmapheresis. The anticoagulative effect is an advantage as a system where the traditional anticoagulative substance like heparin and citrate may be replaced by the displacer substance as herein described.

DEFINITIONS

By the term "deleterious substances" it is herein meant substances having a negative effect on the physiological functions of the body. The deleterious substances are for example uremic toxins.

By the term "displacer substance" it is herein meant substances which binds to protein, for example albumin, and the binding affinity is competitive, or allosteric, or both, with the deleterious substances. Thus the displacer substance may have a stronger affinity to the protein than the deleterious substance, and by that displace the deleterious substance.

BRIEF DESCRIPTION OF THE DRAWING(S)

FIGS. 1a-e shows the result of displacing p-cresol with different displacer substances. In FIG. 1a the measured amount of p-cresol when sodium salicylate was used as displacer molecule is shown. In FIG. 1b, the measured amount of p-cresol displaced when sodium acetylsalicylate was used as displacer substance is shown. In FIG. 1c, the measured amount of p-cresol displaced when sodium octanoate was used as displacer substance. FIGS. 1d and 1e show the measured amount of p-cresol displaced when a combination of displacer substances was used, sodium octanoate and sodium salicylate, and sodium octanoate and sodium acetylsalicylate, respectively.

FIGS. 2a-d shows the result of displacing p-cresol with addition of dialysis solution or water, at different temperatures and pH.

DETAILED DESCRIPTION OF THE INVENTION

The human body consists of approximately 60% water, a level which is important to maintain for its survival. In a healthy body the level of water is self-regulated, by, for example, passage through the kidneys. One task of the normal kidney is to remove superfluous fluid from the blood, such as water, urea and other waste products. The resulting urine is transferred to the bladder and finally leaves the body during urination. The kidneys second task is to regulate for example the balance of electrolytes and acid and base in the body. With malfunctioning kidneys, disorders may develop in most major body organs, a syndrome called uremia. If uremia remains untreated, it will lead to death. Uremia is treated either by kidney transplantation or some form of extracorporeal blood cleaning, e.g. hemodialysis, hemofiltration, hemodiafiltration or peritoneal dialysis.

The waste products are a large number of substances that originate from the body cellular metabolism. Urea is the most abundant waste product and it is produced when the proteins are metabolised. Creatinine is another important waste product that originates from muscle metabolism. In addition to these waste products, other compounds such as protein bound compounds and foreign substances are all excreted into the urine.

In acute kidney failure, the kidneys stop to function and to remove the waste products, the kidney function is lost rapidly and the kidneys loose their ability to remove waste products. In most cases it is only a temporary condition, but may remain and be transferred into a chronic condition.

Uremic toxines constitute a group of substances which are retained in patients with kidney failure and are involved in the development and manifestation of the uremic syndrome. These uremic retention solutes are subdivided into three different groups according to their physical-chemical properties and their behaviour during dialysis therapy or treatment. Small water soluble molecules are molecules with molecular weight less than 500 Dalton (D). Examples are urea and creatinine. These substances are easily removed by dialysis. Middle (or medium) molecules are molecules having a molecular weight range between 500 D and 15000 D, and can be removed by hemodialysis with increased efficacy with high-flux membrane separating.

Protein bound molecules are most often of low molecular weight but are considered as middle or high molecular weight molecules due to their protein binding. Examples are organic anions such as indoxyl sulphate (IS), 3-carboxy-4-methyl-5-propyl-2-furanpropanoic acid (CMPF), p-cresyl sulphate (PCS), p-cresol and hippuric acid (HA).

In a renal patient, the concentration of urea in water is considered to be the same inside and outside of the cells. When urea is removed through dialysis from the plasma water outside the cell a concentration difference occurs across the cell. This, in turn, causes urea to diffuse out of the cell and thus clean the cell. The cell wall is highly permeable to urea and the transport over the cell membrane quick.

However, other substances also to be removed from the blood are not so readily transported over the membrane. When artificial renal procedure, like the dialysis procedures described above is required, also other means are needed to remove these substances from the blood. This applies to the deleterious substances. One reason for this may be that the substances are mainly residing inside the cells. The substances may also be bound to proteins, such as albumin, residing in the plasma. Removal of these substances is therefore a challenge. Protein bound compounds are molecules with low molecular weight, but may be considered as middle and high molecular weight molecules due to their protein binding. They are most often bound to albumin having a molecular weight of 66 kD.

Most of these compounds are biologically and biochemically active and have high toxic activity, for example causing cardio-vascular damage [1,2]. Most of these compounds are organic anions, such as indoxyl sulphate (IS), 3-carboxy-4-methyl-5-propyl-2-furanpropanoic acid (CMPF), p-cresyl sulphate (PCS), p-cresol and hippuric acid(HA). These compounds are transported in the body by organic anion carrier molecules to various tissues. The compounds may be accumulated in the body, for example in the kidneys, in tissues including endothelial cells, vascular smooth muscle cells, osteoblasts, and the central nervous system leading to adverse toxic effect [3]. The role of these compounds in the uremic syndrome has been neglected for long time due to the difficulties to identify them in the uremic serum.

A common characteristic for these compounds is their low clearance by most of the today available dialysis strategies. For removal of these compounds it is only their free fraction that may be removed, thus it is required to remove the compound from the protein before removal. One possibility to remove the protein bound compound, the toxin, is to stimulate their dissociation from the binding protein, such as albumin.

One option for removal of the protein bound toxins is using the competitive binding which can displace the deleterious substances like uremic toxins from their binding sites on the protein, such as albumin. Also allosteric binding is to be considered for this displacement of the deleterious substance.

Another option is to change the pH value and/or temperature to influence the binding between the albumin and the uremic toxins, and by that facilitate the dissociation of the compounds. A further option is a combination of the above, thus using the competitive or allosteric binding and changing the pH value and/or the temperature to influence the binding between the albumin and the uremic toxins.

Human serum albumin (HSA) is the most abundant transporter or carrier protein in plasma. The protein comprises three different domains, (I, II and III) with each domain in turn is subdivided into two-domains, A and B. The high affinity binding sites for ligand binding are located in sub-domains IIA and IIIA, also known as the Sudlow's site I and site II [4].

The albumin present in the plasma contributes to regulate the osmotic pressure and to maintain the pH level of the extravascular fluids. Furthermore, it is an important extracellular antioxidant and is a carrier protein of compounds, such as various endogenous and exogenous compounds (such as fatty acids, hormones, and introduced molecules such as medicinal drugs) to its two major binding sites, namely site I and site II. Further binding sites are also present, for example such binding metals.

The ability of albumin to bind endogenous and exogenous compounds as well as drugs is reduced in chronic kidney failure due to the accumulation and the binding of the uremic toxins to this serum protein [5]. An example, the binding of bilirubin to albumin in patients with CKD is reduced due to the competitive binding of CMPF to the same binding site, site I.

Furthermore, protein bound uremic toxins and drugs compete for the same binding sites on the albumin molecule. Uremic toxins inhibit the binding of many drugs to the serum albumin, for example indoxyl sulphate inhibits albumin binding of some drugs such as diazepam that binds to the binding site (site II). CMPF is a compound which displaces drugs that bind to binding site I of the protein, for example warfarin. The increased concentration of the drug may lead to an enhanced toxic effect on different organs.

The displacer substance included in the invention may be selected from $C_5$-$C_{10}$-fatty acid, or derivatives thereof, or salts thereof; and salicylic acid, derivatives thereof, or salts thereof; or combinations thereof.

It is herein illustrated that $C_5$-$C_{10}$-fatty acids, or salts thereof has an ability as displacer substance, thus having higher affinity to the protein than the deleterious substance like for example p-cresol.

By the term "$C_5$-$C_{10}$-fatty acids" it is herein meant fatty acids with a linear or branched alkyl chain comprising $C_5$-$C_{10}$ carbon atoms. The carbon chain may be further substituted with substituents selected form $C_1$-$C_3$-alkyl (methyl, ethyl or propyl)-groups, -hydroxi (—OH), and —COON. The list is not exhaustive. Examples of $C_5$-$C_{10}$-fatty acids are pentanoic acid (valeric acid), hexanoic acid (caproic acid), heptanoic acid (enanthic acid), octanoic acid (caprylic acid), nonanoic acid (pelargonic acid), and decanoic acid (capric acid). The fatty acids may also be included as salts thereof; an example is sodium salt of the fatty acid.

In one embodiment of the invention is the use of a $C_5$-$C_{10}$-fatty acid, or derivative thereof, or salt thereof, as a displacer substance to remove a deleterious substance bound to a protein illustrated.

An example of fatty acid is octanoic acid, and its sodium salt, sodium octanoate, octanoic acid is also known as caprylic acid. It is to be found in human breast milk, coconut oil as well as in palm oil. Sodium octanoate has an antifungal effect and is used for the treatment and cure of fungus- and yeast infections caused by *Candida albicans*. It is also used as anti-bacterial agent due to its short fatty acid chain that can easily penetrate membranes [6,7]. Sodium octanoate has also useful effects on patient suffering from Crohns' disease, by inhibiting the secretion of interleukin-8 from intestinal epithelial cells and thereby suppressing its inflammatory effect on the intestines [8].

Sodium octanoate can be used as a displacer substance to displace non-covalent binding of p-cresyl sulphate, p-cresol and indoxyl sulphate to albumin Sudlow II binding site [9]. It has been reported in a study that sodium octanoate binds with high affinity to a primary binding site at site II. This binding leads to allosteric change in the binding site II, which in turn results in the displacement of compounds binding there. It can also displace the compounds binding there in a competitive way. The said study showed that sodium octanoate at high concentration can bind to albumin binding site I but with much lower binding affinity, and thereby displaces target solutes than bind to this site in a competitive fashion [10].

Salicylic acid is another displacer substance illustrated herein, also as derivatives thereof, and as salt thereof. Salt of salicylic acid is for example the sodium salicylate, included in the experiments according to the invention. Derivative of salicylic acid is also included in the invention. An example of derivative is acetylsalicylic acid and salts thereof, such as sodium acetylsalicylate. Acetylsalicylic acid is also known as Aspirin® which Is a weak acid and belongs to nonsteroidal anti-inflammatory drugs (NSAIDs). However, acetylsalicylic acid differs from the common NSAIDs by the mechanism of action. Acetylsalicylic acid is an acetyl derivative of salicylic acid. The substance is used as pain relief, as anti-inflammatory agent to suppress inflammation and as an anti-pyretic agent to reduce fever. The substance is also effective as anti-coagulation agent. The substance is also used against cancer.

Combinations of displacer substances are two or more displacer substances selected from the groups of $C_5$-$C_{10}$-fatty acids, or derivatives thereof, or salts thereof; and salicylic acid, derivatives thereof, or salts thereof; or combinations thereof. Examples of combinations are $C_5$-$C_{10}$-fatty acids, or derivatives thereof, or salts thereof, in combination with salicylic acid, or salt thereof. Another example is $C_5$-$C_{10}$-fatty acids, or derivatives thereof, or salts thereof, in combination with acetylsalicylic acid, or salt thereof. Further examples are combination of sodium octanoate and sodium salt of salicylic acid; and combination of sodium octanoate and sodium salt of acetyl salicylic acid. Another example is combination of sodium octanoate, sodium salt of salicylic acid, and sodium salt of acetyl salicylic acid.

By the term "biological fluid" it is herein meant the fluid acting as carrier of the deleterious substances and the protein they are bound to. The biological fluid is to be cleaned from these deleterious substances, and may be, for example, blood, plasma, and peritoneal fluid. The biological fluid is extracorporeal biological fluid. The list of biological fluids is not exhaustive.

By the invention also a cleaning fluid is provided. The cleaning fluid comprises the displacer substances as are herein described. The cleaning fluid is intended to be added in renal treatment like dialysis treatment. The cleaning fluid comprises a displacer substance selected from $C_5$-$C_{10}$-fatty acid, or derivatives thereof, or salts thereof; and, salicylic acid, derivatives thereof, or salts thereof; or combinations thereof. For example the displacer substance is $C_5$-$C_{10}$-fatty acids, derivatives thereof, or salts thereof; salicylic acid, derivatives thereof, or salts thereof; or combinations thereof. The cleaning fluid does also comprise physiologically acceptable excipients and electrolytes. The cleaning fluid comprises the different components in physiologically acceptable concentrations and has pH of between 6.5 and 8.

The displacer substances for removal of deleterious molecules from a biological fluid may be included in a system, for example a system for treatment of biological fluid such as a system for dialysis treatment of blood. The displacer substances may be selected from $C_5$-$C_{10}$-fatty acid, or derivatives thereof, or salts thereof; and salicylic acid, derivatives thereof, or salts thereof; and or combinations thereof.

Also a system configured to remove deleterious substances from an extracorporeal biological fluid, such as blood or plasma. The system may comprise an extracorporeal blood circuit, a fluid circuit and a blood treatment unit comprising a filter system including one or more semipermeable membranes separating a fluid compartment from a blood compartment, provided with means for mixing blood and a cleaning fluid and directing the mixture obtained through said blood compartment, wherein the cleaning fluid comprises displacer substances to remove said deleterious substances bound to protein. The displacer substances are selected from $C_5$-$C_{10}$-fatty acids or salts thereof, or salicylic acid, or derivatives thereof, or salts thereof; or combinations thereof.

Optionally, the system is equipped with an additional unit wherein the biological fluid, for example blood, is separated in a first fraction of blood cells, and a second fraction of plasma. To the second fraction is a displacer substance added for removal of the deleterious substances.

The displacer substances could be administered as regional anticoagulant pre dialyzer, thus before the blood treatment unit in any dialysis machine. Alternatively a separate plasma separation device, such as a plasma separation filter, could be included for a separate treatment of albumin present in plasma with water, displacer substances, or pH adjusted water to further increase the amount of removed deleterious substance, e.g. uremic toxin.

An advantage of administration as regional anticoagulant should be the anti-coagulant properties from salicylic acids and the possibility to decrease the need for heparin administration. An advantage with a plasma separation device is that the removal of uremic toxins could be facilitated by large volumes of water and or adjustment of pH with or without displacer molecules.

It has been shown that removal of deleterious substance shall occur at pH of between 5 and 8, for example between 5 and 7. It has been shown that the affinity of the deleterious substance is decreased and that the affinity of the displacer substance is stronger within this pH range. Example of suitable pH is 5, 5.5, 6, 6.5, 7, 7.5, and 8.

The removal of the deleterious substances is also preferably performed at temperature of between 30 and 60 degree Celsius, more preferably between 35 and 50 degree Celsius. Examples of suitable temperature are 30, 35, 36, 37, 38, 39, 40, 45, 50, 55 and 60 degree Celsius.

The displacer substances describe that release of the deleterious substances bound to the protein is achieved. The separation of these substances from the biological fluid may be performed by techniques like dialysis, electrodialysis, plasmapheresis, etc.

When using the displacer substances that are added during dialysis treatment, the deleterious substances or uremic toxins are separated from the biological fluid via the semipermeable membrane included in the system.

In electrodialysis the ionic substances are forced through the membrane by electric forces. In plasmapheresis, a pressure difference is created across the membrane so that plasma (i.e. plasma water and proteins) flows through the membrane into the second side.

The deleterious substances may also be removed from the biological fluid by a repeated addition of washing liquid. The washing liquid is for example water or dialysis fluid, preferably water. This is especially applicable on the plasma present in the blood, and also carrying the albumin binding the deleterious substances. By adding an excessive amount of water, some of the protein bound deleterious substances are removed from protein and appears free in the solution. In this form it may be easily removed by dialysis treatment of the fluid.

The conformation of the protein, the albumin, is different depending on the pH of the surrounding liquid. The removal of deleterious substances by water shall take place at pH 6-9, preferably at pH between 7 and 9, for example at pH 8.

The method of removing deleterious substances by repetitive addition and removal of water comprises the following steps: a) separating of plasma from blood; b) adjusting the pH of the plasma, for example by adding a base, such as sodium hydroxide (NaOH) or applying a low pressure to degas carbon dioxide; c) adding of washing liquid, adjusted to pH between 6 and 9, for example pH 8; d) washing; e) separating the washing liquid and therein present deleterious substances which has been removed from the protein.

The steps c) to e) are then repeated until no or low amounts of deleterious substance may be detected in the washing liquid of step e). The advantages with this method is that water is cheap and readily available in dialysis machines. Large amounts of water may be used without excess problems of disposal. The method may be combined with high temperature treatment, such as a temperature between 35 and 50 degrees Celsius, and by that amplify the cleaning effect.

EXAMPLES

By way of example, without any limitation of the scope, the following examples identify a variety of parameters pursuant to embodiments of the present invention.

Test of Uremic Toxins

The competitive and allosteric binding properties of displacer substances to protein were investigated. More specifically, different displacer substances capability to displace p-cresol bound to bovine serum albumin was investigated, and described in the following examples. As deleterious substance was p-cresol selected and considered representative for different uremic toxins.

Material and Methods

Centrifugation is performed in a Vivaspin® (Sartorius AG). Vivaspin® is a single tube that consists of two compartments. An upper compartment and a lower compartment separated by a semipermeable membrane. Centrifugation is applied to force the solvent into the lower compartment through the membrane, leaving a more concentrated sample in the upper chamber.

pH measurements were performed with pH meter Orion 420 A.

Standards and Reagents:

Bovine serum albumin (BSA) (Sigma-Aldrich, purity >96%), p-cresol (deleterious substance—uremic toxin), sodium salicylate (displacer substance and anti-coagulant, purity 99.5%), acetylsalicylic acid (displacer substance and anti-coagulant) and sodium octanoate (displacer substance, purity 99%) were purchased from Sigma-Aldrich.

Methanol and Milli-Q water were used (all HPLC grade).

Sodium acetylsalicylate (the salt of acetylsalicylic acid) was prepared by adding sodium hydroxide (NaOH) (2 mol/l) to acetylsalicylic acid (10 g) until the pH value reached 7. The solution of acetylsalicylic acid and NaOH was frozen and the placed in a freeze-drying machine for 16 hours to allow the frozen NaOH to sublimate, leaving only the powder of sodium acetylsalicylate.

Analysis Method: HPLC

A 25 cm×4.6 mm Supelcosil™ LC-18 column with particle size 5 μm was used. Mobile phase A consisted of Milli-Q water and mobile phase B was methanol. The analytical method was isocratic with 50% of mobile phase A and 50% mobile phase B at a flow rate of 1 ml/min. The column temperature was 25 C and the injection volume was 20 μL. The uremic solute (p-cresol) was quantified by using a diode array detector (DAD). The detector was monitored at wavelengths of 280 nm and 254 nm. The optimal UV absorption for p-cresol occurred at 280 nm. A standard curve for p-cresol at three different concentrations (0.005 mg/ml, 0.02 mg/ml and 0.04 mg/ml) was used for all p-cresol analyses.

Sample Preparation p-cresol: Stock solutions at a concentration of 1 mg/ml were prepared by dissolving p-cresol in distilled water (Milli-Q). Working standard solutions were prepared by appropriate dilution of the stock solutions with Milli-Q water. Three different concentrations of p-cresol were prepared and analysed by the HPLC to estimate the retention time and absorbance for p-cresol:

Normal blood concentration of p-cresol: 0.005 mg/ml
Uremic blood concentration of p-cresol: 0.02 mg/ml
Maximum uremic concentration of p-cresol: 0.04 mg/ml.

Following Tests were Performed:

Example A: Test of p-cresol binding to albumin (BSA)
Example B: Test of p-cresol binding to albumin (BSA) in presence of displacer substances
Example C: Test of pH influence on the samples of Example B
Example D: Test of influence of both temperature and pH
Example E: Test of different temperature
Example F: Test of p-cresol binding to albumin together with combination of two displacer substances
Example G: Test of p-cresol binding to albumin together with displacer substances.
Example H: Addition of dialysis fluid to a mixture of BSA and p-cresol
Example I: Addition of water to a mixture BSA and p-cresol
Example J: Test of influence of water.
Example K: Test of influence of water at high temperature Example A Binding of p-cresol to Albumin at Different pH Values The ability of p-cresol, in different concentrations, to bind to the protein (bovine serum albumin, BSA) was tested. The concentration of BSA was kept at the level as in normal blood (40 mg/ml). The components were mixed in water and centrifuged in a Vivaspin® (Sartorius AG) to remove protein at 5700 rpm for 60 minutes at room temperature.

The samples prepared are presented in Table 1.

TABLE 1

The p-cresol concentration of samples prepared:

| Sample: | BSA (mg/l) | P-cresol (mg/ml) |
| --- | --- | --- |
| A1 | 40 | 0.005 |
| A2 | 40 | 0.02 |
| A3 | 40 | 0.04 |
| A4 | 40 | 0.01 |

Samples were prepared by preparing samples of 1 ml containing 40 mg/ml BSA and 0.02 mg/ml p-cresol (sample A2 of table above) with pH of 5, 7 and 8, respectively. pH was adjusted by addition of sodium hydroxide (NaOH) or hydrochloric acid (HCl) to the solutions, as appropriate. The pH of the samples was measured before centrifugation and analysis by the HPLC.

The effect of pH on the binding of p-cresol to BSA is presented in Table 2

TABLE 2 sample A2 tested at different pH

| pH | Measured concentration of p-cresol (mg/ml) |
| --- | --- |
| 5 | 0.0002 |
| 7 | 0.0032 |
| 8 | 0.0037 |

At pH 5 substantially no free p-cresol was detected, thus all p-cresol was considered bound to BSA. While at pH 7 and 8 an amount of unbound p-cresol was detected, and it was concluded that at higher pH the binding of p-cresol to the BSA is weakened. The weakening of the binding of p-cresol to BSA at pH 7 and 8 is probably due to the conformational change that the protein undergoes in pH range of 6 to 9, breakage of van der Waals interactions between the p-cresol and BSA occurred. Thus, a conformational change from N to B (from neutral to base) could be concluded. Further, more p-cresol was dissociated from albumin at high pH value, especially pH 8.

Example B

Test of p-cresol Binding to Albumin (BSA) in Presence of Displacer Substances

Samples were prepared by dissolving BSA in water to a concentration similar blood (40 mg/ml). p-Cresol was added to obtain an uremic concentration (0.02 mg/ml) and displacer substances in varying concentrations (10, 100, and 200 mg/ml).

The displacer substances included in the examples are sodium salicylate, sodium octanoate and sodium acetylsalicylate.

The mixed solutions were centrifuged to remove protein at 5700 rpm for 70 minutes at room temperature before analysis. The pH was adjusted to 7 (physiological pH) by addition of NaOH to the samples. The samples were injected into a HPLC. The measurement of p-cresol by HPLC analysis was performed at room temperature.

The samples prepared are presented in Table 3. Also the results, as measured p-cresol concentration (mg/ml) are presented in the Table 3.

TABLE 3

| Sample | BSA (mg/ml) | p-cresol (mg/ml) | Sodium salicylate (mg/ml) | Sodium octanoate (mg/ml) | Sodium acetylsalicylate (mg/ml) | Measured p-cresol concentration mg/ml |
| --- | --- | --- | --- | --- | --- | --- |
| B | 40 | 0.02 | 0 | 0 | 0 | 0.0032 |
| B1a | 40 | 0.02 | 10 | 0 | 0 | 0.0048 |
| B1b | 40 | 0.02 | 100 | 0 | 0 | 0.0070 |
| B1c | 40 | 0.02 | 200 | 0 | 0 | 0.0078 |
| B2a | 40 | 0.02 | 0 | 10 | 0 | 0.0032 |
| B2b | 40 | 0.02 | 0 | 100 | 0 | 0.0060 |
| B2c | 40 | 0.02 | 0 | 200 | 0 | 0.0072 |
| B3a | 40 | 0.02 | 0 | 0 | 10 | 0.0032 |
| B3b | 40 | 0.02 | 0 | 0 | 100 | 0.0043 |
| B3c | 40 | 0.02 | 0 | 0 | 200 | 0.0067 |

Sodium salicylate has a competitive effect on the binding of p-cresol to the protein (BSA). It can be concluded that, the higher the concentration of sodium salisylate used in the samples, the higher is the concentration of free p-cresol. This means that sodium salicylate competes with p-cresol for its binding site (more specifically site II of the protein) with the effect that p-cresol is inhibited to bind to the albumin. Furthermore, sodium salicylate can also bind to other sites on the albumin (e.g. site I) and induce an allosteric changes in the region of site II, resulting in the displacement of p-cresol binding there. Therefore, it was concluded that sodium salicylate acts as a displacer substance and able to displace p-cresol from its binding site on the protein.

The results of Sample B1a-B1c in Table 3 show that a fraction of free p-cresol may be detected. The concentration of unbound p-cresol increases as the concentration of sodium salicylate is enhanced. The concentration of BSA was 40 mg/ml and of p-cresol was 0.02 mg/ml in all samples. The pH was kept at 7.

Further, the results of Samples B2a-B2c show that an amount of p-cresol is unbound from the protein due to the presence of the sodium octanoate which displaces p-cresol from its binding site on the albumin. The concentration of free p-cresol is increased with the concentration of sodium octanoate. Sodium octanoate binds with higher affinity to site II of the protein than to site I. The p-cresol may be directly displaced or an allosteric change may be induced in the site II region and p-cresol from site II may occur. In Example B2c precipitation occurred.

Further, from the results of Samples B2a-B2c it may also be observed that free p-cresol can be detected when the concentration of sodium octanoate is 10 mg/ml and 100 mg/ml. Also here the pH was kept at 7.

In a corresponding way, the results of Sample B3a-B3c, thus p-cresol and sodium acetylsalicylate, shows that sodium acetylsalicylate competes with p-cresol in its binding with the protein. The higher concentration of sodium acetylsalicylate, the more free p-cresol is detected in the sample. Sodium acetylsalicylate may also bind to other sites and induce allosteric change of site II. By the result it is confirmed that sodium acetylsalicylate displace p-cresol from its binding site on the albumin.

The results of Samples B3a-B3c shows that free p-cresol can be detected when the concentration of sodium acetylsalicylate is at least between 10 and 100 mg/ml at pH 7.

Example C

Test of pH Influence on the Samples of Example B

The influence of the pH value on the binding affinity of the p-cresol and the binding competitors to the bovine serum albumin (BSA) was investigated. The selected pH were pH 5, 6, 8 and 9. The pH was adjusted by adding sodium hydroxide (NaOH) or hydrochloric acid (HCl). The tests were performed with the following displacer substances: sodium salicylate, sodium octanoate and sodium acetylsalicylate. The results show and confirm that the pH is important parameter which influences the binding affinity of p-cresol and the displacer substances. The displacement of p-cresol by the binding competitors is enhanced at specific pH values. The effect of pH on the binding affinity agrees with the expected effect because the albumin undergoes a conformation change (from N to B form) of the protein in the pH range 6 to 9. At pH 5 the albumin exists in the N form. The results are present in Table 4

TABLE 4

| Sample: | B1a | B1b | B1c | B2a | B2b | B2c | B3a | B3b | B3c |
|---|---|---|---|---|---|---|---|---|---|
| Component: | | | | | | | | | |
| Albumin (BSA) | 40 | 40 | 40 | 40 | 40 | 40 | 40 | 40 | 40 |
| p-cresol (mg/ml) | 0.02 | 0.02 | 0.02 | 0.02 | 0.02 | 0.02 | 0.02 | 0.02 | 0.02 |
| Sodium salicylate (mg/ml) | 10 | 100 | 200 | 0 | 0 | 0 | | | |
| Sodium ctanoate (mg/ml) | | 0 | | 10 | 100 | 200 | | | |
| Sodium acetyl salicylate (mg/ml) | | 0 | 0 | 0 | 0 | | 10 | 100 | 200 |
| Measured p-cresol concentration ($\times 10^{-3}$ mg/ml) at pH: | | | | | | | | | |
| pH 5 * | 7.3 | 14.7 | 17.2 | 8.6 | — | — | 6.8 | 10.0 | — |
| pH 7 | 4.8 | 7.0 | 7.8 | 6.0 | 7.2 | — | 4.3 | 6.7 | — |
| pH 8 | 2.0 | 0.2 | 0.2 | 3.5 | 4.9 | 8.5 | 0.2 | 3.2 | — |
| pH 9 | — | — | — | 0.2 | 1.0 | 5.8 | — | — | — |

* pH 6 for B2a

In Table 4 the result and the effect of pH on the binding of sodium salicylate and p-cresol to BSA is presented. The amount of unbound p-cresol is enhanced at low pH, especially at pH 5. Thereby, more p-cresol is displaced from its binding site on the BSA by sodium salicylate. This may depend on that the albumin conformation at pH 5, thus in its N-form, can bind sodium salicylate with higher affinity. Increased pH, and the binding affinity of sodium salicylate to BSA decreases because the BSA undergoes a conformational change (from N to B form). It is concluded that BSA in its N form binds sodium salicylate stronger than in its B form. At lower pH, pH 4, precipitation occurred. At pH 8, substantially no effect was observed, probably due to the conformation of the protein, the B-form, binds sodium salicylate with lower affinity.

Further, the result for sodium acetylsalicylate is presented. The concentration of free p-cresol was highest when the concentration of sodium acetylsalicylic acid was 200 mg/ml and pH 5. Substantially no p-cresol could be detected at pH 8.

Also, the result of the study of how pH may alter the binding affinity of p-cresol and sodium octanoate to BSA is presented in Table 4 (Sample B2a-B2c). The concentration of free p-cresol was shown to increase in the solution having low pH when sodium octanoate was present. With increased pH, the amount of unbound p-cresol decreases and p-cresol remained unbound to the bovine serum albumin (BSA). This effect is most probably depending on a conformational change of the protein in the pH range of 6 to 9. At pH 6 the protein is in N form. It was assumed that the protein binds more sodium octanoate in this conformation resulting in the displacement of p-cresol form its binding sites on the albumin. At higher pH, pH values higher than 6 the albumin starts to exist more in the B form. At this pH the binding affinity is lower for sodium octanoate. At pH 5 precipitation of the solution was observed. Precipitation occurred in solutions with concentration of sodium octanoate of 100 mg/ml and 200 mg/ml at pH 6.

In Table 4 (Sample B3a-3c) corresponding result for sodium acetylsalicylate is presented. It is shown how the binding affinity between p-cresol and sodium acetylsalicylicate to bovine serum albumin is altered by different pH. Solution comprising sodium acetylsalicylate with concentration of 200 mg/ml was not included due to precipitation.

It is shown that more p-cresol is removed from its binding sites on the BSA at low pH when sodium acetylsalicylate is present. As pH increases the amount of unbound p-cresol is decreased. This may be due to that albumin in the N form has a higher binding affinity to sodium salicylate and sodium octanoate. Albumin in N-form has a higher binding affinity to sodium acetylsalicylate, which in turn can displace more p-cresol. The binding weakens as the pH increases, due to the conformational change to the B-form of the protein.

Further, it is shown that the amount of unbound, free p-cresol increases as the concentration of sodium acetylsalicylate is enhanced. The concentration of BSA was 40 mg/ml and the concentration of p-cresol was 0.02 mg/ml in all samples tested.

Example D

Influence of Temperature and pH

The influence of the combination of temperature and pH on the binding affinity of p-cresol to the bovine serum albumin (BSA) in the presence of binding competitors was studied. The pH in the samples was adjusted before the centrifugation at 50° C. (heating cabinet).

The tests performed regarding the influence of temperature and pH are presented in Table 5.

TABLE 5

| Example | BSA (mg/ml) | p-cresol (mg/ml) | Sodium salicylate (mg/ml) | Sodium octanoate (mg/ml) | Sodium acetylsalicylate (mg/ml) |
| --- | --- | --- | --- | --- | --- |
| D1 | 40 | 0.02 | 0 | 0 | 0 |
| D2 | 40 | 0.02 | 100 | 0 | 0 |
| D3 | 40 | 0.02 | 0 | 100 | 0 |
| D4 | 40 | 0.02 | 0 | 0 | 100 |

The pH of each sample was adjusted in accordance with the results obtained in Example A and Example C to maximize the effect at the used concentration.

The result of Example D1 to D4 is presented in Table 6.

The measured concentration of p-cresol as a function of the concentration of binding competitors at specific pH values was investigated, and the effect of temperature on the binding affinity of p-cresol and of the binding competitors to the bovine serum albumin (BSA). The effect of temperature was clearly indicated; more p-cresol is displaced from its binding site on the albumin by the binding competitors at temperature of 50° C. compared with room temperature.

TABLE 6

Test of influence of high temp and varying pH

| Example | pH | Measured p-cresol concentration (mg/ml) at room temperature | Measured p-cresol concentration (mg/ml) at 50° C. |
| --- | --- | --- | --- |
| D1 | 8 | 0.0037 | 0.0065 |
| D2 | 5 | 0.017 | 0.017 |
| D3 | 8 | 0.0049 | 0.014 |
| D4 | 7 | 0.0067 | 0.010 |

Example E

Combination of Displacer Substances at Different Temperature

A combination of two different binding competitors was investigated for synergetic effect. Following compositions were tested:

TABLE 7

| Composition | BSA (mg/ml) | p-cresol (mg/ml) | Sodium salicylate (mg/ml) | Sodium octanoate (mg/ml) | Sodium acetylsalicylate (mg/ml) |
| --- | --- | --- | --- | --- | --- |
| E1 | 40 | 0.02 | 10 | 10 | 0 |
| E2 | 40 | 0.02 | 0 | 10 | 10 |

The compositions were tested at room temperature and at elevated temperature of 50° C. for investigating the influence of temperature on the binding affinity of p-cresol and the binding competitors to the bovine serum albumin (BSA). pH was adjusted to pH 6 (in accordance with the results obtained in Example C.

A combination of two binding competitors has a better effect on the removal of p-cresol from its binding site on the albumin than a single binding competitors acting alone on the binding site of the protein. The pH is adjusted to 6 in all samples because as explained in the previous mentioned results that the amount of free p-cresol increases as the pH decreases in the presence of the binding competitors. Furthermore, more p-cresol dissociate from the albumin when it is heated.

TABLE 7

The measured amount of p-cresol in presence of two displacer substances is present

| | Measured amount of p-cresol (mg/ml) at room temperature | Measured amount p-cresol (mg/ml) at 50° C. |
| --- | --- | --- |
| Composition E1 | 0.014 | 0.020 |
| Composition E2 | 0.012 | 0.019 |

Substantially no free p-cresol was detected in the absence of binding competitors.

For examples (F, G, H and I) below a solution (stock solution) having concentration of 1 mg/ml was prepared by dissolving p-cresol (5 mg) in distilled water (Milli-Q) (5 mg). The BSA solution was prepared from a different batch of BSA than previous preparation (Example A). Impurities in the BSA could be concluded in the present BSA. Different concentrations of p-cresol were prepared from the stock solution:

Normal blood concentration of p-cresol: 0.005 mg/ml

Uremic blood concentration of p-cresol: 0.02 mg/ml

Maximum uremic concentration of p-cresol: 0.04 mg/ml

Example F

Combination of Displacer Substances

A combination of two different binding competitors was used to investigate the properties of the combination. Following solutions were made:

| Example | BSA (mg/ml) | p-cresol (mg/ml) | Sodium salicylate (mg/ml) | Sodium octanoate (mg/ml) | Sodium acetylsalicylate (mg/ml) |
|---|---|---|---|---|---|
| F1 | 40 | 0.02 | 10 | 10 | 0 |
| F2 | 40 | 0.02 | 0 | 10 | 10 |
| F1-blank | 40 | 0 | 10 | 10 | 0 |
| F2-blank | 40 | 0 | 0 | 10 | 10 |

The experiments were performed at temperature of 37° C. and an adjusted pH value of 6.

Example G

Test of Different Displacer Substances

Solutions of bovine serum albumin with normal blood concentration 40 mg/ml, p-cresol with the uremic concentration 0.02 mg/ml and 10 mg/ml of the binding competitors (sodium salicylate, sodium octanoate, and sodium acetylsalicylate) were prepared. Solutions comprising a combination of displacer substances were prepared (10 mg/ml of sodium salicylate in combination with 10 mg/ml of sodium octanoate; 10 mg/ml of sodium octanoate in combination with 10 mg/ml sodium acetylsalicylate). The pH of the samples was adjusted to pH 5, 5.3, 5.6, and 5.9, respectively. The amount of p-cresol displaced in each sample was measured with HPLC as above. The result is presented in FIGS. 1a-1e.

These examples confirm the experiments performed in Examples A-E wherein another BSA was used.

From the results presented in Example I and FIG. 1a-1e, the same conclusion as presented in previous examples can be drawn. It has been shown that the binding affinity is changed by differing the pH.

Example H

Addition of Dialysis Fluid to a Mixture of BSA and p-cresol

A solution containing 0.02 mg/ml p-cresol and 40 mg/ml bovine serum albumin (BSA) were centrifuged (Vivaspin®) for 20 minutes until 0.5 ml was removed and analyzed. Then, 0.5 ml dialysis solution (SelectBag One diluted with 37 mmol/l sodium bicarbonate and 103 mmol/l NaCl) is added to the remaining 0.5 ml solution (p-cresol and BSA) in the centrifuge (Vivaspin) and centrifuged during 20 minutes until 0.5 ml was removed for the analysis. This procedure was repeated until no p-cresol could be detected by the HPLC.

The same procedure was repeated with the solution comprising no added p-cresol. The tests were performed at pH 8 and room temperature. The results are presented in FIG. 2a.

Example I

Addition of Water to a Mixture BSA and p-cresol 1 ml of solution containing 0.02 mg/ml p-cresol and 40 mg/ml bovine serum albumin at pH 8 was centrifuged at temperature of 37° C. (heating cabinet) for 20 minutes until 0.5 ml was removed and analysed. Then 0.5 ml water (Milli-Q) was added to the remaining 0.5 ml solution (p-cresol and BSA) in the centrifuge (Vivaspin®) and centrifuged again until 0.5 ml was removed for the analysis. This procedure was repeated 20 times, until no p-cresol could be detected by the HPLC. The pH was adjusted to 8.

The tests were performed at pH 8 and 37° C.

The results are presented in FIG. 2b.

Example J

Test of Influence of Water, Addition of Water to Mixture of BSA and p-cresol at pH 8

The influence of water addition on the binding affinity of p-cresol to bovine serum albumin was investigated in this example, performed at room temperature. 1 ml of a solution comprising 0.02 mg/ml p-cresol and 40 mg/ml bovine serum albumin (BSA) was centrifuged (Visaspin®) for 20 minutes. 0.5 ml of the solution was removed and analysed.

0.5 ml water (Milli-Q quality) was added to the remaining 0.5 ml solution (p-cresol and BSA) and centrifuged (in Vivaspin®) for another 20 minutes before another 0.5 ml was removed for the analysis. This procedure was repeated 16 times, until no p-cresol could be detected by the HPLC (calculated amount 0.01989 mg). This means that almost 100% of the added p-cresol is removed from the binding sites on BSA. The addition of water influences the binding of peresol to BSA by breaking the van der Waals interactions between p-cresol and BSA. Furthermore, water sets the equilibrium between the bound and the unbound p-cresol leading to the removal of an amount of the bound p-cresol from its binding site when a new equilibrium is adjusted after the addition of water.

The pH value in the stock solution (BSA and p-cresol) was chosen and adjusted in accordance with the result in Example A to maximize the effect.

The results are presented in FIG. 2c.

Example K

Addition of Water to Mixture of Protein and p-cresol at High Temperature (pH 8)

The previous experiment was repeated at elevated temperature. A 1 ml solution containing 0.02 mg/ml p-cresol and 40 mg/ml bovine serum albumin (BSA), pH 8, was centrifuged (Vivaspin®) at 50° C. for 20 minutes until 0.5 ml was removed and analysed. Then 0.5 ml water (Milli-Q) was added to the remaining 0.5 ml solution comprising p-cresol and BSA, centrifuged for 20 minutes until 0.5 ml was removed for the analysis. This procedure was repeated 20 times, and no p-cresol could be detected by the HPLC. The pH was adjusted to 8 in the solution as the most effective binding affinity was observed at this pH value (Example A).

The p-cresol was measured after each repetition. The measured amount of p-cresol was 0.027 mg, thus more than the added amount of p-cresol. It was concluded that some degradation of the sample occurred at high temperature under action of water. It may also indicate that contaminations of the proteins have the same retention time as p-cresol because the retention time shifted towards lower value after 5 ml was used. Furthermore, it may also be due to integration faults in the system. About 100% of the p-cresol is considered unbound after addition of 5 ml water and the remaining parts are contaminations.

The results are presented in FIG. 2d.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

REFERENCES

[1] Barreto F. C., Barreto D. V., Liabeuf C., Meert N., Glorieux G., Temmar M., Choukroun G., Vanholder R., Massy Z. A., (2009), Serum indoxyl sulphate is associated with vascular disease and mortality in chronic kidney disease patients. Clin. J. Am. Soc. Nephrol. 4:1551-1558.

[2] Meijers B. K., Claes K., Bammens B., de Loor H., Viaene L., Verbeke K., Kuypers D., Vanrenterghem Y., Evenepoel P., (2010), p-Cresol and cardiovascular risk in mild-to-moderate kidney disease. Clin. J. Am. Soc. Nephrol, 5:1182-1189.

[3] Enomoto A, Niwa T., (2007), Roles of organic anion transporters in the progression of chronic renal failure. Ther Apher Dial. 11:27-31.

[4] Meijers B J I, Bammens B., Verbeke K., Evenepoel P., (2008) A review of albumin binding in CKD, Am J Kidney Dis. 51:839-850.

[5] Toshiaki S., Keishi Y., Tomoko S., Ulrich K. H., Ayaka S., Masaki O. (2001) Interaction Mechanism Between Indoxyl Sulfate, a Typical Uremic Toxin Bound Site II, and Ligands Bound to Site I of Human Serum Albumin. Pharmaceutical Research 18:520-524.

[6] Beare-Rogers J., Dieffenbacher A., Holm J. V. (2001). Lexicon of lipid nutrition (IUPAC technical report). Pure and applied Chemistry 73: 685-744.

[7] www.chemspider.com/Chemical-Structure.15307.html. Retrieved on 20 Apr. 2012.

[8] Hoshimito A., Suzuki Y., Katsuno T., Nakajima H., Saito Y. (2002). Caprylic acid and medium-chain triglycerides inhibit IL-8 gene transcription in Caco-2 cells: comparison with the potent histone deacetylase inhibitor trichostatin A. Br. J. Pharmacol. 136:280-6.

[9] De Loor H., Meijers B K, Meyer T W, Bammens B., Verbeke K., Dehaen W., Evenepoel P. (2009) Sodium octanoate to reverse indoxyl sulfate and p-cresyl sulfate albumin binding in uremic and normal serum during sample preparation followed by fluorescence liquid chromatography. J Chromatogr A. 1216: 4684-8.

[10] Noctor T A., Wainer I W., Hage D S., (1992), Allosteric and competetive displacement of drugs from human serum albumin by octanoic acid, as revealed by high-performance liquid affinity chromatography, on a human serum albumin-based stationary phase. J. Chromatogr. 577:305-15.

The invention claimed is:

1. A method of removing a deleterious substance bound to a protein in an extracorporeal biological fluid comprising:
   a) introducing a displacer substance into the biological fluid under conditions in which the displacer substance displaces deleterious substance bound to the protein, thereby resulting in additional unbound deleterious substances in the biological fluid; and
   b) removing unbound deleterious substance from the biological fluid,
   wherein the displacer substance is a combination of sodium octanoate with one or both of sodium salicylate and sodium acetylsalicylate.

2. A method according to claim 1, wherein the step a) and step b) are performed at a temperature of between 30 and 60 degrees Celsius.

3. A method according to claim 1, wherein the step a) and step b) are performed at pH of between 5 and 8.

4. A method according to claim 1, wherein the biological fluid is blood; blood plasma; or peritoneal fluid.

5. A method according to claim 1, wherein the step b) is performed by any one or more of the methods comprising dialysis, electrodialysis or plasmapheres.

* * * * *